United States Patent [19]
Oxendine, Jr.
[11] 4,343,299
[45] Aug. 10, 1982

[54] STABILIZING APPARATUS FOR MALE AND FEMALE PARTNERS

[76] Inventor: Luther C. Oxendine, Jr., Rte. 2, Box 63, Maxton, N.C. 28364

[21] Appl. No.: 249,148

[22] Filed: Mar. 30, 1981

[51] Int. Cl.³ .............................................. A61M 19/00
[52] U.S. Cl. ...................................... 128/1 R; 128/31; 128/134; 2/44
[58] Field of Search .................... 128/1 R, 31, 79, 134; 2/44

[56] References Cited

U.S. PATENT DOCUMENTS

| | | | |
|---|---|---|---|
| 412,999 | 10/1889 | Turney | 128/31 |
| 1,098,492 | 6/1914 | Gibson | 2/44 |
| 1,722,192 | 7/1929 | Brokaw | 2/44 |
| 2,594,097 | 4/1952 | Twyman | 128/1 R |
| 3,046,982 | 7/1962 | Davis | 128/134 |
| 3,896,787 | 7/1975 | Withers | 128/1 R |

*Primary Examiner*—Dalton L. Truluck
*Attorney, Agent, or Firm*—B. B. Olive

[57] ABSTRACT

A strap apparatus is adapted for mounting on and use by male and female partners during coitus to stabilize the actions of each.

1 Claim, 3 Drawing Figures

STABILIZING APPARATUS FOR MALE AND FEMALE PARTNERS

DESCRIPTION

1. Cross Reference to Related Application

This application relates to patent application Ser. No. 178,688, deposited Aug. 18, 1980, now abandoned entitled "Super Saddle".

2. Technical Field

The invention relates to devices employed by male and female partners during sexual activities and particularly to body-mounted strap devices for such purpose.

3. Background Art

Various devices and apparatus have been devised for enhancing sexual enjoyment between male and female partners during coitus. However, so far as is known by applicant, no one has heretofore proposed a strap arrangement adapted for use by male and female partners during coitus to provide resilient foot support for the male and a stabilizing effect for both partners.

Independent of the use to which body strap devices have heretofore been applied, it is recognized that strap devices as such have been previously devised to assist in bracing the back or to assist in lifting objects. Some of such strap devices have incorporated shoulder, abdomen and leg straps as in U.S. Pat. No. 1,371,690. Also, such body strap devices have utilized elastic strap members as in U.S. Pat. No. 1,098,492. Other types of body straps are illustrated in U.S. Pat. Nos. 975,454; 1,678,584 and 1,722,192. However, none of such strap devices so far as is known to applicant has been designed for or adapted to stabilize male and female partners during coitus and the provision of such a device becomes the object of the invention.

DISCLOSURE OF THE INVENTION

The invention provides a strap arrangement to be worn during coitus and incorporates for the female partner shoulder and abdomen straps and for the male partner a pair of leg straps having elastic bands adapted for use as resilient stirrups during coitus.

BEST MODE FOR CARRYING OUT THE INVENTION

Figure 1:
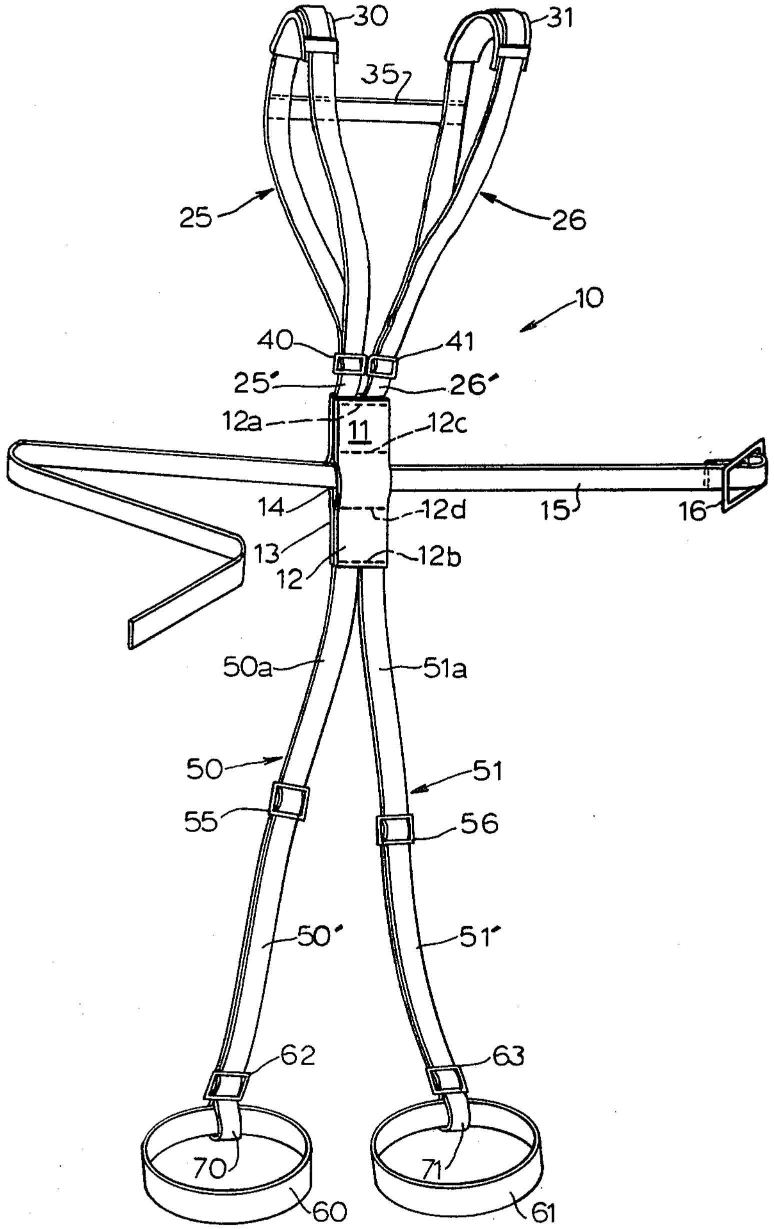
FIG. 1 is a perspective view of the strap apparatus of the invention removed from the male and female partners for whom it is intended to be used.

The strap apparatus 10 of the invention comprises an inelastic back pad 11 preferably made of two mated pieces 12, 13 of rectangular shaped canvas-like strap material sewn together at one end by stitch line **12*a*, at an opposite end by stitch line 12*b* and in an intermediate portion by a pair of spaced apart stitch lines 12*c*, 12*d* providing an aperture 14. An abdomen strap 15 for the female partner is loosely received in a slidable relation in aperture 14 and includes a buckle 16 for adjustable tightening thereof around the abdomen of the female partner 20** as illustrated.

During the sewing of pad 11 one end of each of two inelastic adjustable shoulder straps 25, 26 for the female partner is sewn by the laterally extending stitch line **12*a* into the upper end of pad 11 in laterally spaced positions. Slidable shoulder pads 30, 31 are provided for comfort and slide on the loop portions of the respective straps 25, 26. A short elastic back strap 35 is secured between the back runs of straps 25, 26. The upper loop portions of straps 25, 26 are made adjustable by use of sliding clamps 40, 41 which are secured to the terminal ends of the straps 25, 26 and slide on the respective front strap runs 25′, 26′**.

The sewing of pad 11 is also arranged so that the lateral stitch line **12*b* engages one end of each of two inelastic adjustable stirrup support straps 50, 51 which, as best seen in FIG. 1, are sewn into the lower end of pad 11 in laterally spaced positions for use by the male partner. Straps 50, 51 provide adjustable loop portions 50′, 51′ whose lengths are controlled by use of sliding clamps 55, 56 which are secured to the respective terminal ends of the straps 50, 51 and slide on the respective strap runs 50*a*, 51*a*.**

A pair of heavy, closed loop elastic bands 60, 61 are loosely mounted in the loop ends 50′, 51′ of the male partner's stirrup support straps 50, 51 and provide in effect a pair of resilient stirrups for receiving the feet of the male partner during coitus. Stirrup bands 60, 61 are retained in position by means of sliding strap retainers 62, 63.

Figure 2:
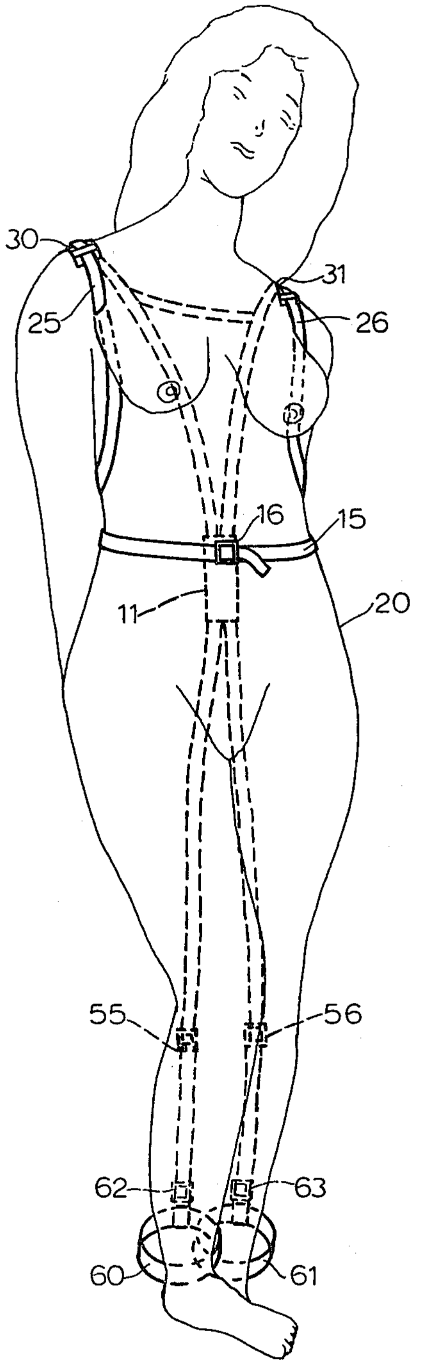
FIG. 2 is a front view.
Figure 3:
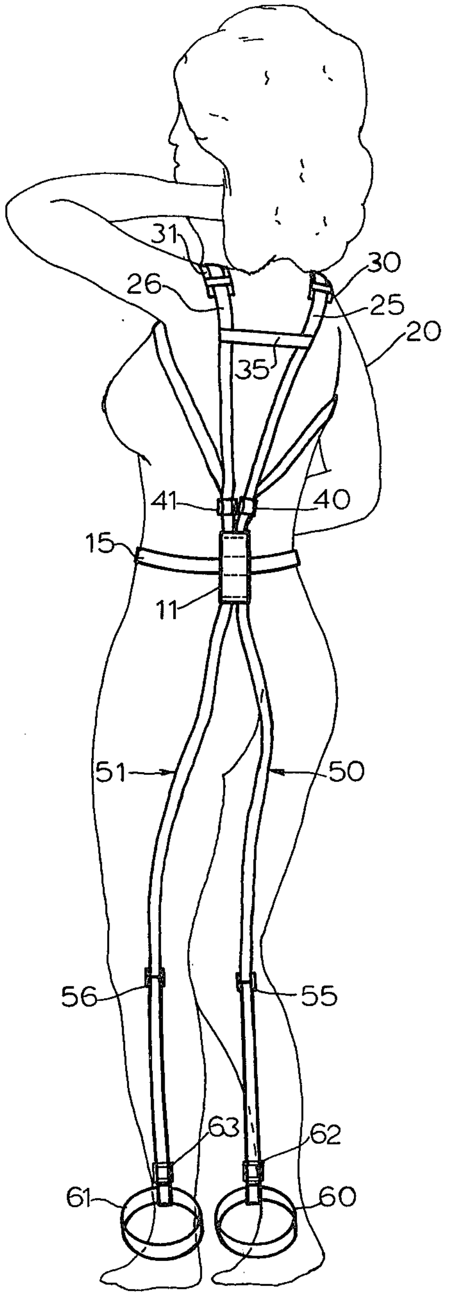
FIG. 3 is rear view of a human female partner in a vertical position with the strap apparatus of the invention preparatory to coitus.

In use, the female partner mounts the strap apparatus 10 in the manner illustrated in FIGS. 2 and 3 with proper adjustments being made by means of buckle 16 and sliding clamps 40, 41. The partners then assume the desired position for coitus and the male partner places his feet in the stirrups 60, 61 and makes proper adjustments for length in the leg straps 50, 51 using the sliding clamps 55, 56. Appropriate adjustments are also made in the retaining strap clamps 62, 63 as required to secure stirrups 60, 61 substantially secure in the outer extreme loop portions 70, 71 of straps 50, 51. In use, the back pad 11 is held in the lower lumbar curve of the back of the female partner in a central lengthwise extending position as illustrated. The relative fixed positioning of back pad 11 is, of course, assisted by the abdomen strap 15 and the shoulder straps 30, 31 so that during coitus the male partner is forced to perform against the resilient forces asserted by the stirrups 60, 61 and assert such forces on the female partner through pad 11. An overall stabilizing effect of the partner's positioning during coitus is achieved.

I claim:

1. A stabilizing apparatus for male and female partners comprising:

(a) an inelastic rectangular flexible back pad formed of mated stitched together pieces having a laterally extending tubular portion formed by lateral stitching intermediate the length thereof and adapted for placement in a central lengthwise of the body extending position in the lower lumbar curve of he back of the female partner and to conform with the shape thereof;

(b) an inelastic strap passing loosely through said tubular portion of said pad and adapted with adjustable securing means to encircle the abdomen of said female partner for maintaining said pad secured to said curve of said female partner's back;

(c) a pair of inelastic shoulder loop straps having the loop ends thereof secured by stitching in a spaced apart relation to an upper end portion of said pad and adapted with adjustable securing means mounted on each of the respective front loop portions thereof to be adjustably mounted on and passed under the shoulders of said female partner;

(d) a shoulder pad positionably mounted on each of said shoulder loop straps;

(e) an elastic cross strap secured by stitches to and extending between respective back loop portions of said shoulder loop straps and adapted in use to extend across the back of said female partner above the location of said pad and below the location of said shoulder pads; and (f) a pair of strap assemblies for use by the said male partner, each said assembly comprising:

(i) an inelastic strap having one upper end integrally secured by stitching to the lower end edge of said pad and spaced apart from the other such assembly elastic strap and having an opposite lower end formed as a first strap loop means with means for adjusting the length of said first strap loop and to an extent at least sufficient to accommodate to the normal leg and foot positions of said male partner during coitus;

(ii) a closed elastic strap loop adapted as a stirrup for receiving one foot of said male partner; and (iii) means for releasably locking the lower loop end of said first strap loop to retain said closed elastic strap loop positioned therein, whereby during use each of said partners' positioning is stabilized by action of said apparatus and each leg of said male partner is forced to act against the resilient force of said elastic strap loops utilizing the same as elastic stirrups for the feet of said male partner.

* * * * *

UNITED STATES PATENT AND TRADEMARK OFFICE

CERTIFICATE OF CORRECTION

PATENT NO. : 4,343,299

DATED : August 10, 1982

INVENTOR(S) : Luther C. Oxendine, Jr.

It is certified that error appears in the above—identified patent and that said Letters Patent is hereby corrected as shown below:

Col. 2, line 57, correct "he" to read --the--

Signed and Sealed this

*Nineteenth* Day of *October 1982*

[SEAL]

*Attest:*

GERALD J. MOSSINGHOFF

*Attesting Officer*

*Commissioner of Patents and Trademarks*